(12) United States Patent
Xie et al.

(10) Patent No.: US 11,739,053 B2
(45) Date of Patent: Aug. 29, 2023

(54) P62-ZZ CHEMICAL INHIBITOR

(71) Applicant: ID4PHARMA, LLC, Pittsburgh, PA (US)

(72) Inventors: Xiang-Qun Xie, Sewickley, PA (US); Garson David Roodman, Indianapolis, IN (US); Kyaw-Zeyar Myint, Ashland, MA (US); Noriyoshi Kurihara, Pittsburgh, PA (US)

(73) Assignee: ID4PHARMA, LLC, Pittsburgh, PA (US)

( * ) Notice: Subject to any disclaimer, the term of this patent is extended or adjusted under 35 U.S.C. 154(b) by 903 days.

(21) Appl. No.: 16/365,532

(22) Filed: Mar. 26, 2019

(65) Prior Publication Data

US 2020/0031761 A1    Jan. 30, 2020

Related U.S. Application Data

(63) Continuation of application No. 14/727,710, filed on Jun. 1, 2015, now abandoned, which is a continuation (Continued)

(51) Int. Cl.
| | |
|---|---|
| *C07C 229/36* | (2006.01) |
| *C07D 309/40* | (2006.01) |
| *C07C 211/50* | (2006.01) |
| *C07C 317/34* | (2006.01) |
| *C07C 217/58* | (2006.01) |
| *C07C 217/76* | (2006.01) |
| *C07C 219/06* | (2006.01) |
| *C07D 241/44* | (2006.01) |
| *C07C 229/14* | (2006.01) |
| *C07D 487/04* | (2006.01) |
| *C07C 235/48* | (2006.01) |
| *C07C 251/76* | (2006.01) |

(Continued)

(52) U.S. Cl.
CPC .......... *C07C 229/36* (2013.01); *A61K 31/137* (2013.01); *A61K 31/15* (2013.01); *A61K 31/216* (2013.01); *A61K 31/351* (2013.01); *A61K 31/495* (2013.01); *A61K 31/498* (2013.01); *A61K 31/519* (2013.01); *A61K 45/06* (2013.01); *C07C 211/50* (2013.01); *C07C 217/58* (2013.01); *C07C 217/76* (2013.01); *C07C 219/06* (2013.01); *C07C 229/14* (2013.01); *C07C 235/48* (2013.01); *C07C 249/16* (2013.01); *C07C 251/76* (2013.01); *C07C 317/34* (2013.01); *C07D 241/44* (2013.01); *C07D 309/32* (2013.01); *C07D 309/40* (2013.01); *C07D 475/08* (2013.01); *C07D 487/04* (2013.01); *C12N 5/0693* (2013.01)

(58) Field of Classification Search
None
See application file for complete search history.

(56) References Cited

PUBLICATIONS

Hiruma et al., Blood vol. 113, Issue 20, May 2009 (Year: 2009).*

(Continued)

*Primary Examiner* — Karl J Puttlitz

(74) *Attorney, Agent, or Firm* — Dentons Cohen & Grigsby P.C.

(57) ABSTRACT

A method for treating a p62-mediated disease (e.g., multiple myeloma) in a subject, the method comprising administering to the subject a therapeutically effective amount of at least one p62-ZZ inhibitor compound.

17 Claims, 12 Drawing Sheets

Related U.S. Application Data of application No. 14/237,494, filed as application No. PCT/US2012/049911 on Aug. 8, 2012, now Pat. No. 9,580,382.

(60) Provisional application No. 61/521,287, filed on Aug. 8, 2011.

(51) Int. Cl.
*A61K 31/137* (2006.01)
*A61K 31/351* (2006.01)
*A61K 31/495* (2006.01)
*A61K 31/519* (2006.01)
*A61K 31/15* (2006.01)
*A61K 31/498* (2006.01)
*A61K 45/06* (2006.01)
*C07C 249/16* (2006.01)
*C07D 309/32* (2006.01)
*C07D 475/08* (2006.01)
*C12N 5/09* (2010.01)
*A61K 31/216* (2006.01)

(56) References Cited

PUBLICATIONS

Silbermann et al., Blood, vol. 128, Issue 22, Dec. 2016 (Year: 2016).*

Klopman et al., Molecular Pharmacology Aug. 1, 1997, 52 (2) 323-334 (Year: 1997).*

* cited by examiner

P62-ZZ CHEMICAL INHIBITOR

CROSS REFERENCE TO RELATED APPLICATIONS

This application is a continuation application of U.S. patent application Ser. No. 14/727,710 filed Jun. 1, 2015, pending, which is a continuation application of U.S. patent application Ser. No. 14/237,494 filed Feb. 12, 2015, which issued as, U.S. Pat. No. 9,580,382, on Feb. 28, 2017, which is a 35 U.S.C. 371 National Stage application of International Application No. PCT/US2012/49911, filed Aug. 8, 2012, which claims the benefit under 35 U.S.C. § 119(e) of U.S. Provisional Application No. 61/521,287, filed Aug. 8, 2011. The disclosure of each of the prior applications is considered part of and is incorporated by reference in the disclosure of this application.

BACKGROUND

Multiple myeloma (MM) is an incurable hematologic malignancy, characterized by the dysregulated proliferation of plasma cells and progressive bone destruction in up to 80% patients. Despite the introduction of novel and more potent treatment regimens including thalidomide and bortezomib, MM is still the second most prevalent hematological malignancy. As reported by the Leukemia & Lymphoma Society (Facts 2009-2010), both the MM patient number and new diagnosed cases have markedly increased each year. Therefore, novel therapeutics that effectively inhibits tumor growth and overcome conventional drug resistance are urgently needed.

SUMMARY

One embodiment disclosed herein is a method for treating a p62-mediated disease in a subject, the method comprising administering to the subject a therapeutically effective amount of at least one p62-ZZ inhibitor compound.

Also disclosed herein is a method of modulating p62 activity in stromal cells, comprising contacting stromal cells with a compound, or a pharmaceutically acceptable salt or ester thereof, having a formula I as described below in the Detailed Description section.

A further embodiment disclosed herein is a method of inhibiting multiple myeloma cell growth, comprising contacting multiple myeloma cells with at least one p62-ZZ inhibitor compound. Further disclosed herein is a compound, or a pharmaceutically acceptable salt or ester thereof, having a formula I of:

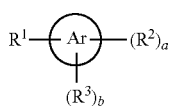

wherein Ar is an arylene or heteroarylene;
$R^1$ has a structure of:

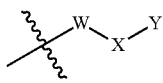

wherein W is an alkanediyl, alkenediyl, a carbonyl, or a combination thereof;
X is —$NR^5$—, wherein $R^5$ is H or an alkyl, or —O—; and
Y is a hydroxyalkyl, an amino alkyl, or a carboxylalkyl;
each $R^2$ is the same or different and has a structure of:

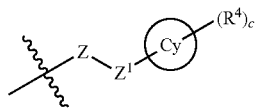

wherein Z is —$NR^6$—, wherein $R^6$ is H or an alkyl, —O—, —S—, or $CH_2$—;
$Z^1$ is (—$CH^2$—)$_m$ wherein m is 0 to 5, or an alkenediyl having 2 to 6 carbon atoms;
Cy is a 3-8-membered cycloalkyl, heterocycloalkyl, aryl or heteroaryl ring; and
each $R^4$ is the same or different and is selected from hydroxy, halogen, substituted or unsubstituted alkoxy, substituted or unsubstituted alkyl, or amino; and c is 0 to 5; and each $R^3$ is the same or different and is selected from hydroxy, halogen, substituted or unsubstituted alkoxy, substituted or unsubstituted alkyl, amino, substituted or unsubstituted cycloalkyl, substituted or unsubstituted heterocycloalkyl, substituted or unsubstituted aryl, or a nitro, wherein a is 2 to 5, and b is 0 to 3.

provided that the compound is not:

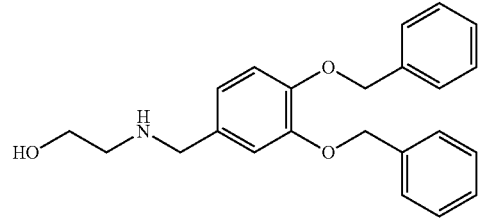 [SMILES: OCCNCc1ccc(OCc2ccccc2)c(OCc2ccccc2)c1]

According to another embodiment, there is disclosed a pharmaceutical composition comprising at least one pharmaceutically acceptable additive, and a compound, or a pharmaceutically acceptable salt or ester thereof, having a formula I as described below in the Detailed Description section.

The foregoing will become more apparent from the following detailed description, which proceeds with reference to the accompanying figures.

BRIEF DESCRIPTION OF THE DRAWINGS

FIG. 4B. MTT assay of CD138(+) primary myeloma cells. Data are shown as mean±SD (n=5). FIG. 4C. Effects of p62-ZZ inhibitors on human stromal cell growth. Primary human stromal cells (5×10³/well) were cultured with 10 μM of p62-ZZ inhibitor (#1-6) containing 10% FCS in IMDM for 48 hours. Stromal cells growth was assayed by MTT assay. Data are shown as the mean±SD (n=5). *P<0.01 compared to vehicle treated culture.

FIG. 5B. IL-6 production by human and mouse marrow stromal cells by ELISA. Normal human and mouse marrow stromal cells were cultured with/without TNFα and p62-ZZ inhibitors (#1-6) for 48 hours. The cell culture media were collected and IL-6 production measured using an IL-6 ELISA kit (R &D). Data are shown as the means (n=2).

FIG. 7B. Human OCL formation. Non-adherent mononuclear cells (2.5×10⁷ cells/10-cm dish) derived from human bone marrow samples were cultured in α-MEM containing 10% FCS, 100 pg/ml recombinant human GM-CSF(R & D) for 7 days. Then the cells were collected and plated (cell density is 1.0×10⁶ cells/nil) in α-MEM containing 20% horse serum with 1 ng/ml TNFα. Half-media changes were performed twice a week containing various concentrations of the p62-ZZ inhibitor #3. The cultures were incubated for a total of 2 weeks at 37° C. with 5% $CO_2$ and 95% humidity. The osteoclasts were stained with the 23C6 antibody which recognizes CD51/61. Data are shown as the mean±SD (n=5). *P<0.01 compared to vehicle treated cultures. 7C. OCL formation by wild type and p62-/- mouse osteoclast precursors. Data is shown as the mean±SD (n=4). *: P<0.01 compared to no-inhibitor cultures.

FIG. 9B. Detection of Apoptosis using the TUNEL reaction with MM1.S cells treated with p62-ZZ antagonist. MM1.S cells were treated with 10/μM of p62-ZZ antagonist #3 for 24 hours and then the cells were collected and mounted on glass slides using the cytospin procedure. Terminal deoxynucleotidyl transferase nick end labeling (TUNEL) reactions were conducted using an In Situ Cell Death Detection Kit (Roche) according to the manufacturer's instructions. The stained cells were analyzed using a fluorescence microscope equipped with standard green filter. FIG. 9C. The p62-ZZ antagonist induced Reactive Oxygen Species in MM1.S cells. MM1.S cells were treated with 10 μM of p62-ZZ antagonist #3 for 6 hours. Cells were collected and stained for Reactive Oxygen Species (ROS) using a Total ROS detection kit (Enzo) according to the manufacturer's instructions.

FIG. 10B. Mean body weights of mice during multidose MTD study. Data are shown as mean±SD for 5 mice. FIG. 10C. Median body weight of mice during multidose MTD study. FIG. 10D. Plasma concentrations p62-ZZ antagonist in pilot mice after 100 mg/kg IV.

DETAILED DESCRIPTION

Overview

Figure 1:
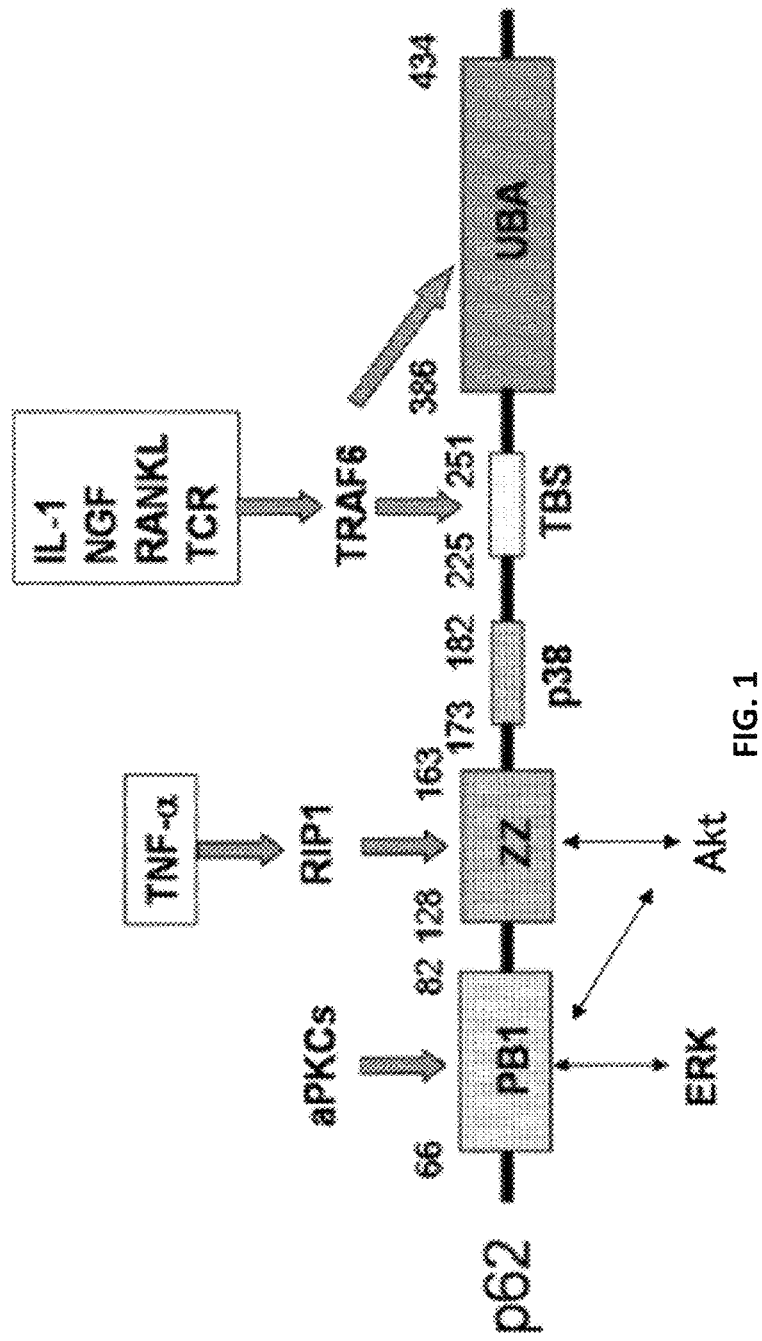
FIG. 1 is a schematic showing various signaling pathways.

Described herein are new p62-ZZ inhibitors that affect, for example, stromal cells and multiple myeloma cells. The novel p62-ZZ inhibitors may demonstrate micromolar (~2 μM) inhibition activity against multiple myeloma cell growth without toxicity to normal stromal cells. In certain embodiments, the compounds are selective p62-ZZ inhibitors meaning that the compounds exhibit inhibition activity that is selective for the ZZ domain relative to other p62 domains.

Sequestosome 1 (p62) plays a key role in the formation of signaling complexes that result in NF-κB, p38 MAPK and PI3K activation in the marrow microenvironment of patients with MM. In contrast to treating subjects with inhibitors of each of the multiple signaling pathways activated in marrow stromal cells by MM cells (e.g., NF-κB or p38 MAPK), blocking the function of p62 should inhibit the activation of the multiple pathways mediated by p62 and have a broader effect on the bone marrow microenvironment.

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Also, as used herein, the term "comprises" means "includes."

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Alkanediyl" refers to a divalent group of the general formula —C—$H_{2n}$— derived from aliphatic, hydrocarbons. A lower alkanediyl has 1 (also referred to as a methylene radical) to 10 carbon atoms, more particularly 1 to 5 carbon atoms.

"Alkenediyl" refers to a divalent group formed from alkanes by removal of two hydrogen atoms from the same carbon atom, the free valencies of which are part of a double bond. A lower alkenediyl has 2 to 10 carbon atoms, more particularly 1 to 5 carbon atoms.

The term "alkenyl" refers to a hydrocarbon group of 2 to 24 carbon atoms and structural formula containing at least one carbon-carbon double bond. A "lower alkenyl" group has 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkylaryl" refers to a group in which an alkyl group is substituted for a hydrogen atom of an aryl group. An example is —Ar—R, wherein Ar is an arylene group and R is an alkyl group.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aminoalkyl" refers to alkyl groups as defined above where at least one hydrogen atom is replaced with an amino group (e.g, —CH$_2$—NH$_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H).

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure.

The term "aralkyl" refers to a group in which an aryl group is substituted for a hydrogen atom of an alkyl group. An example of an aralkyl group is a benzyl group.

The term "aryl" refers to any group derived from an aromatic group including, but not limited to, a benzene ring or to an optionally substituted benzene ring system fused to one or more optionally substituted benzene rings. A "heteroaryl group" is defined as an aryl group that has at least one heteroatom incorporated within the ring of the aryl group.

Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted. Examples of an aryl group include, but are not limited to, phenyl, 2-naphthyl, 1-naphthyl, 1-anthracenyl, and the like.

The term "arylene" refers to a divalent or higher valency benzene ring group or a divalent or higher valency benzene ring system fused to one more optionally substituted benzene rings. The arylene group can be substituted with one or more groups including, but not limited to, alkyl, alkynyl, alkenyl, aryl, halide, nitro, amino, ester, ketone, aldehyde, hydroxy, carboxylic acid, or alkoxy, or the arylene group can be unsubstituted. Examples of an arylene group include, but are not limited to, phenylene (e.g., benzene-1,4-diyl), naphthalene-1,8-diyl, benzenetriyl, benzenetetrayl, and the like.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative": In chemistry, a derivative is a compound that is derived from a similar compound or a compound that can be imagined to arise from another compound, for example, if one atom is replaced with another atom or group of atoms. The latter definition is common in organic chemistry. In biochemistry, derivative refers to compounds that at least theoretically can be formed from the precursor compound.

"Drug-resistant" or "multidrug-resistant" refers to a cancer that is resistant to treatment by at least one therapeutic agent historically administered to treat that cancer. These recurrent cancers often occur after surgery, primary chemotherapy treatment, radiotherapy, or immunotherapy. In certain embodiments, the cancer is a chemotherapeutic-resistant carcinoma.

The terms "halogenated alkyl" or "haaloalkyl group" refer to an alkyl group as defined above with one or more hydrogen atoms present on these groups substituted with a halogen (F, Cl, Br, I).

The term "hydroxyl" is represented by the formula —OH.

The term "hydroxyallcyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

The term "neoplasm" refers to an abnormal cellular proliferation, which includes benign and malignant tumors, as well as other proliferative disorders.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

"Optional" or "optionally" means that the subsequently described event or circumstance can but need not occur, and that the description includes instances where said event or circumstance occurs and instances where it does not.

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters that include a carboxyl group include $C_{1-6}$ alkoxymethyl esters for example methoxy-methyl, $C_{1-6}$ allcanoyloxymethyl esters for example pivaloyloxymethyl, phthalidyl esters, $C_{3-8}$ cycloalkoxycarbonyloxy, $C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and Q.6 alkoxycarbonyloxyethyl esters for example 1-methoxycarbonyl-oxyethyl which may be formed at any carboxy group in the compounds.

An in vivo hydrolysable ester containing a hydroxy group includes inorganic esters such as phosphate esters and α-acyloxyallcyl ethers and related compounds which as a result of the in vivo hydrolysis of the ester breakdown to give the parent hydroxy group.

Examples of a-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), diallcylaminoacetyl and carboxyacetyl. Examples of substituents on benzoyl include morpholino and piperazino linked from a ring nitrogen atom via a methylene group to the 3-or 4-position of the benzoyl ring.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

"Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

The term "subject" includes both human and veterinary subjects.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer, particularly a metastatic cancer.

Inhibitors

Unless context clearly indicates otherwise, all compounds described herein may be provided as a pharmaceutically acceptable salt or ester thereof. In some embodiments, the inhibitor is not a salt or ester. In some embodiments, the inhibitor is a salt. In some embodiments, the inhibitor is an ester. In certain embodiments, the inhibitors may be low molecular weight compounds ("LMWCs", having a molecular weight of less than about, for example and not by way of limitation, 600 daltons).

Disclosed herein are compounds that are p62-ZZ inhibitors having a formula I of:

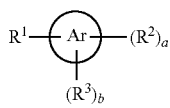

wherein Ar is an arylene or heteroarylene group;
$R^1$ has a structure of:

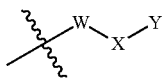

wherein W is an alkanediyl, alkenediyl, a carbonyl, or a combination thereof;
X is —$NR^5$—, wherein $R^5$ is H or an alkyl, or —O—; and
Y is a hydroxyalkyl, an amino alkyl, or a carboxylalkyl;
each $R^2$ is the same or different and has a structure of:

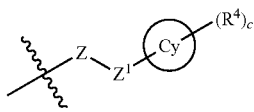

wherein Z is —$NR^6$—, wherein $R^6$ is H or an alkyl, —O—, —S—, 01-$CH^2$—;
$Z^1$ is (—$CH_2$—)m wherein m is 0 to 5, or an alkenediyl having 2 to 6 carbon atoms;
Cy is a 3-8-membered cycloalkyl, heterocycloalkyl, aryl or heteroaryl ring; and
each $R^4$ is the same or different and is selected from hydroxy, halogen, substituted or unsubstituted alkoxy, substituted or unsubstituted alkyl, or amino; and c is 0 to 5; and
each $R^3$ is the same or different and is selected from hydroxy, halogen, substituted or unsubstituted alkoxy, substituted or unsubstituted alkyl, amino, substituted or unsubstituted cycloalkyl, substituted or unsubstituted heterocycloalkyl, substituted or unsubstituted aryl, or a nitro, wherein a is 2 to 5, and b is 0 to 3.

Ar, for example, may be a benzenetriyl (e.g., a benzene-1,3,4-triyl) or a benzenetetrayl.

W, for example, may be a lower alkanediyl, or a lower alkenediyl, or a lower alkanediyl that also includes a carbonyl, or a lower alkenediyl that also includes a carbonyl. X, for example, may be —$NR^5$—, wherein $R^5$ is a lower alkyl, which may be optionally substituted. Y, for example, may be a hydroxyalkyl, an aminoalkyl, or a carboxylalkcyl wherein the alkyl group includes 1 to 4 carbon atoms. In certain embodiments, $R^1$ is —$CH_2$—X—($CH_2$)2-RU, wherein X is NH or O, and $R^{11}$ is hydroxy, carboxyl, substituted carboxyl, or amino (e.g., —$NH_2$).

In certain embodiments, $R^2$ has a structure of;

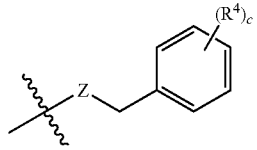

Z, for example may be —$NR^6$—, where in $R^6$ is a lower alkyl, which may be optionally substituted. $R^4$, for example, may be —F, —Cl, —$OCH_3$, —OH, or —$NH_2$.

$R^3$, for example, may be —F, —Cl, —$OCH_3$, —OH, or —$NH_2$. In certain embodiments, $R^3$ is a lower alkyl, a lower alkoxy, $C_1$-$C_4$ alkyl amino (the $C_1$-$C_4$ alkyl moiety of the alkylamino may be straight-chained or branched), di ($C_1$-$C_4$ alkyl)amino, $C_3$-$C_7$ cycloalkyl (particularly $C_3$-CS cycloalkyl, especially cyclopropyl), a hydroxyl-substituted $C_3$-$C_7$ cycloalkyl, a 3 to 6-membered heterocycloalkyl which contains at least one heteroatom selected from N, O and S; an alkyl-substituted 3 to 6-membered heterocycloalkyl, a hydroxyl-substituted 3 to 6-membered heterocycloalkyl, or aryl such as phenyl, naphthyl or anthracenyl, or a nitro group.

In certain embodiments, a is 2, 3, 4 or 5. In preferred embodiments, a is 2. In certain embodiments, a first $R^2$ group is in a meta position on the Ar ring relative to the $R^1$ group, and a second $R^2$ group is in a para position on the Ar ring relative to the $R^1$ group. In certain embodiments, each $R^2$ group has the same structure.

In certain embodiments, b is 0, 1, 2 or 3.
In certain embodiments, c is 0, 1, 2, 3, 4 or 5.
In more particular embodiments, the p62-ZZ inhibitor is selected from:

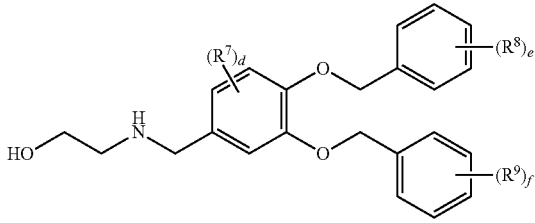

wherein each of $R^7$, $R^8$, and $R^9$ are the same or different and are selected from —F, —Cl, —$OCH^3$, —OH, or —$NH^2$;
d is 0 to 3; e is 0 to 5; and f is 0 to 5;

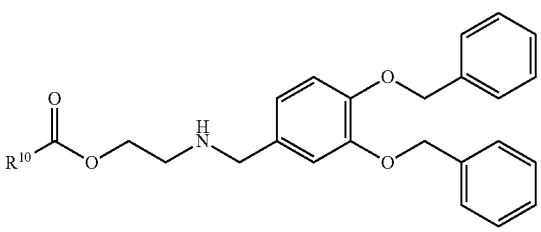

wherein R¹⁰ is an alkyl, particularly a lower alkyl;
wherein n is 1 to 10, more particularly 1 to 5;
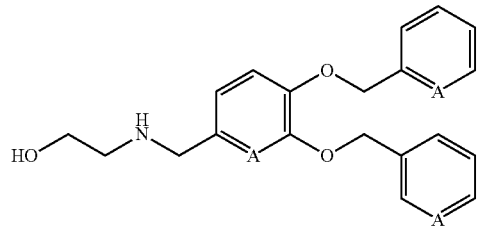
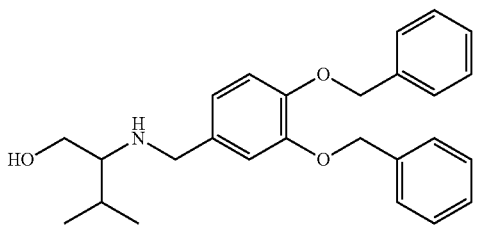
wherein each A is the same of different and are selected from C, O, or N, provided that at least one A is O or N;
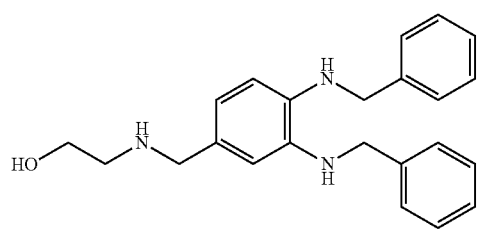
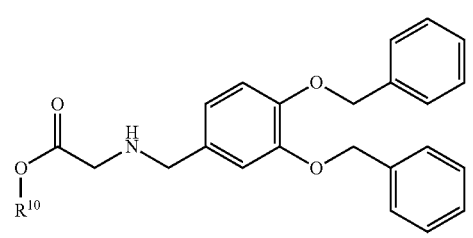
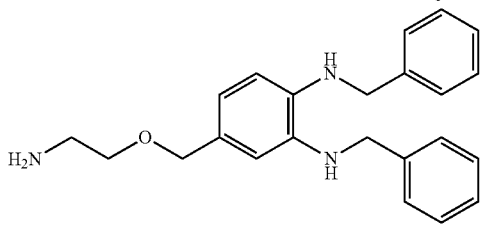
wherein R¹⁰ is an alkyl, particularly lower alkyl;
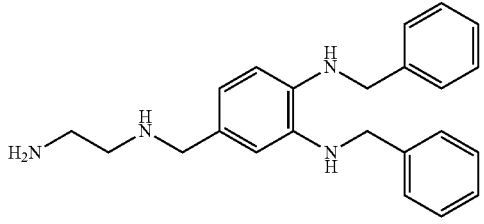
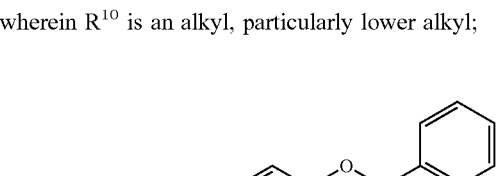
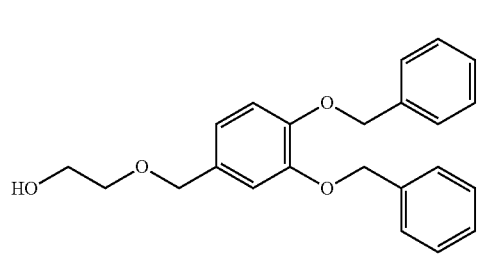
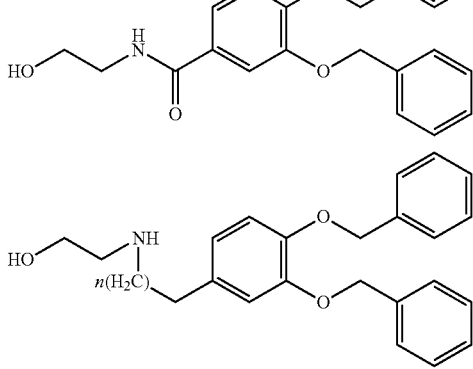
Wherein n is 1 to 10, more particularly 1 to 5;
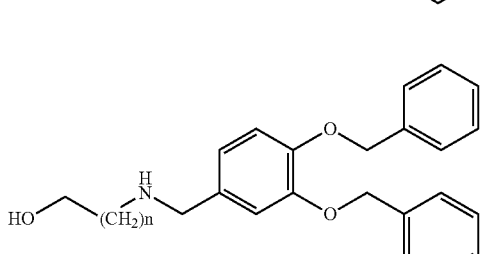
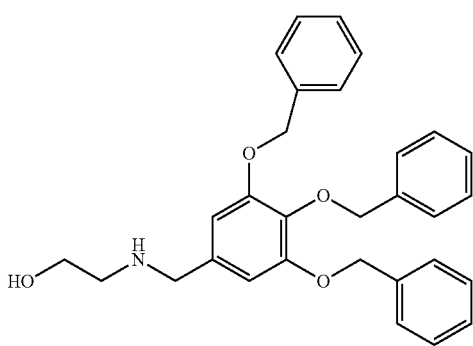

15
-continued
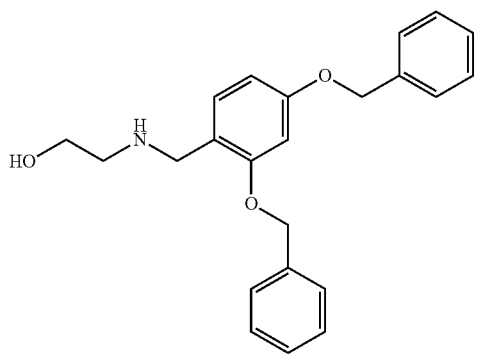
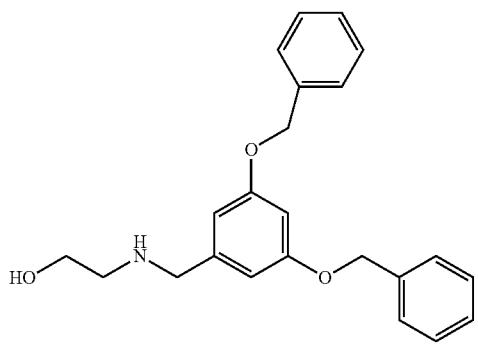
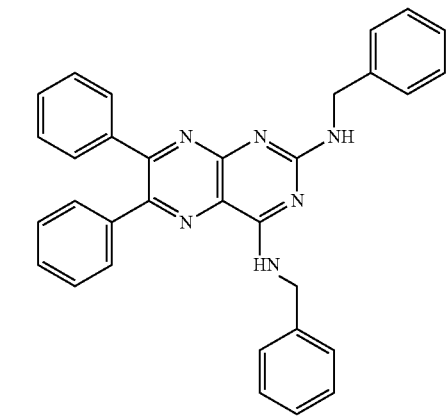
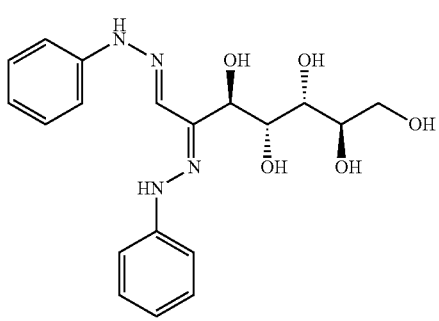
16
-continued
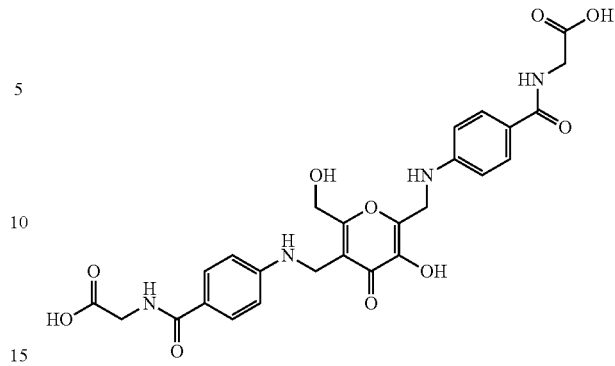
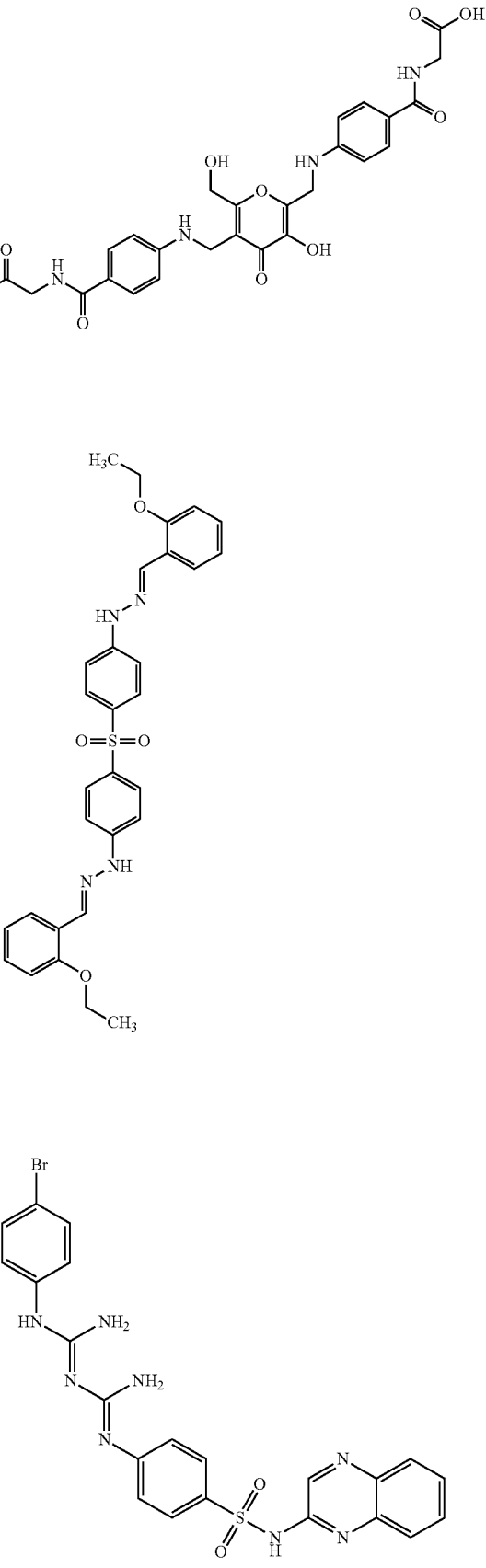

The compounds disclosed herein may be synthesized by techniques known in the art. For example, inhibitor compound 3 may be synthesized as follows:

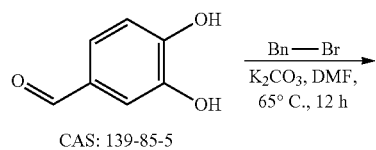

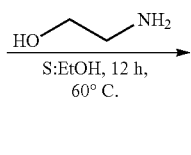

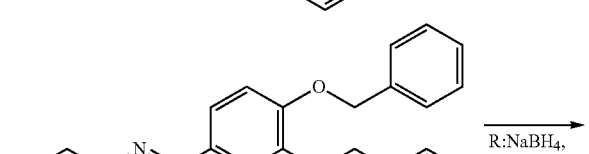

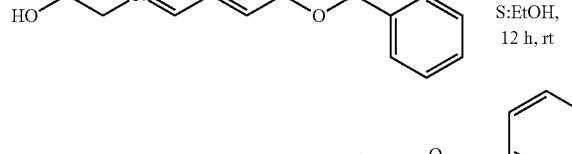

1. Procedure for Synthesis of Compound 3:

3,4-Bis(benzyloxy)benzaldehyde (3.18 g, 10 mmol) was dissolved in dry ethanol, and ethanolamine (0.61 g, 10 mmol) was added. The reaction mixture was stirred for 12 h at 60° C. The reaction solution was cooled down to r.t. NaBH$_4$ (0.57 g, 15 mmol) was added slowly in portions, and the resulting solution was stirred for another 12 h. The solvent was evaporated in vacuo, and the residue was dissolved in water and extracted with EA. The organic layers were combined and dried with NaSO$_4$, filtered, and evaporated in vacuo. The residue was purified by flash column to generate the desired product (1.0 g, 28%).

$^1$H NMR (CDCl$_3$): 7.52-7.33 (m, 10H), 7.01-6.84 (m, 3H), 5.20 (s, 2H), 5.17 (s, 2H), 3.71 (s, 2H), 3.64 (t, J=4.8, 2H), 2.93 (s, 2H), 2.72 (t, J=4.8, 2H).

2. Synthesis of Analogs:

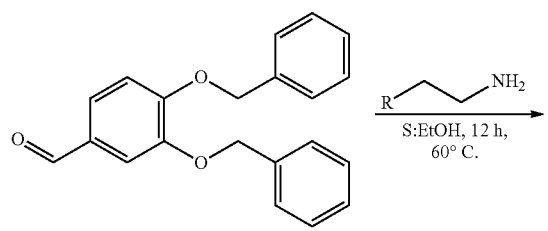

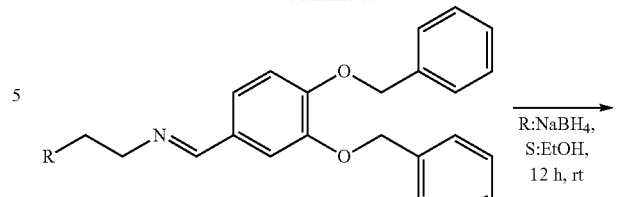

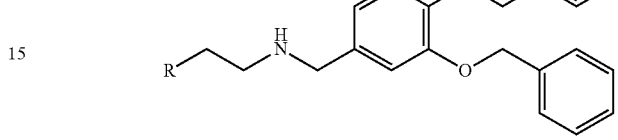

Replace OH group with R=CH$_3$COO—, —NH$_2$, —OCH$_3$, —Cl. Procedure is the same as described for compound 3.

3. Synthesis of Analogues:

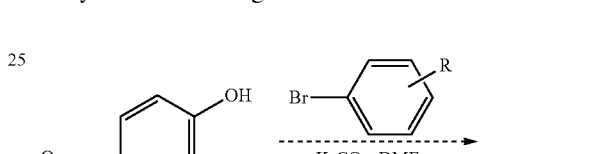

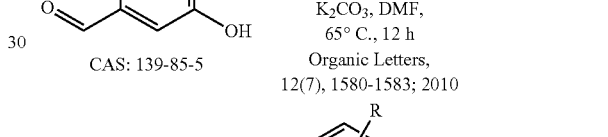

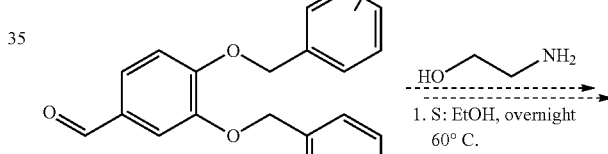

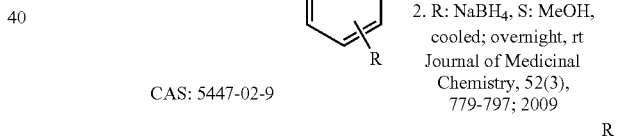

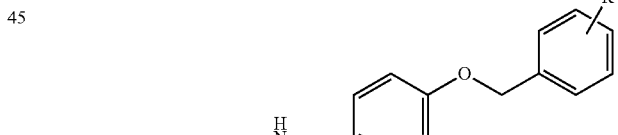

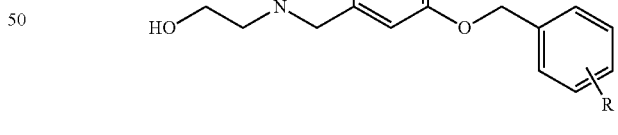

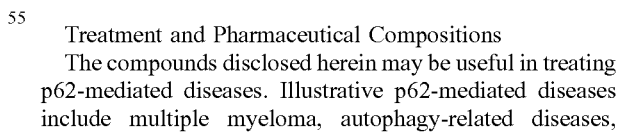

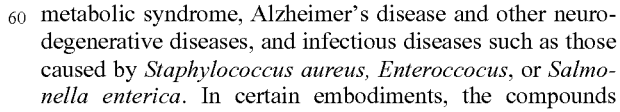

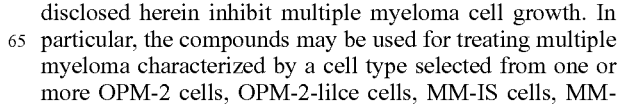

Treatment and Pharmaceutical Compositions

The compounds disclosed herein may be useful in treating p62-mediated diseases. Illustrative p62-mediated diseases include multiple myeloma, autophagy-related diseases, metabolic syndrome, Alzheimer's disease and other neurodegenerative diseases, and infectious diseases such as those caused by *Staphylococcus aureus, Enteroccocus*, or *Salmonella enterica*. In certain embodiments, the compounds disclosed herein inhibit multiple myeloma cell growth. In particular, the compounds may be used for treating multiple myeloma characterized by a cell type selected from one or more OPM-2 cells, OPM-2-lilce cells, MM-IS cells, MM- IS-like cells, MM.1R cells, MM-1R-like cells, KMS-18 cells, KMS-18-like cells, S6B45 cells, 56B45-lilce cells, MR20 cells, MR20-like cells, ARD cells and/or ARD-like cells, Depending on the type of tumor and the development stage of the disease, anticancer effects of the methods of treatment include, but are not limited to, inhibition of tumor growth, tumor growth delay, regression of tumor, shrinkage of tumor, increased time to regrowth of tumor on cessation of treatment, slowing of disease progression, and prevention of metastasis. It is expected that when a method of treatment is administered to a subject in need of such treatment, said method of treatment will produce an effect, as measured by, for example, the extent of the anticancer effect, the response rate, the time to disease progression, or the survival rate. In particular, the methods of treatment are suited for human patients, especially those who are relapsing or refractory to previous chemotherapy, although first line therapy is also envisaged. For example, the compounds disclosed herein may be used for treating cancer, particularly drug-resistant multiple myeloma, that is resistant to one or more of dexamethasone, alkylating agents (e.g., melphalan, cyclophosamide), anthracyclines (e.g., doxorubicin), thalidomide, lenalidomide, CC-4047, bortezomib, and multitargeted kinase inhibitors. The compound disclosed herein may also be co-administered with any of the above-referenced agents. The compounds disclosed herein may block autophagy. Blocking autophagy can enhance the efficacy of a DNA damaging agent for treatment of cancer (Suppression of autophagy by FIP200 deletion impairs DNA damage repair and increases cell death upon treatments with anti-cancer agents. Bae et al., Jl. Mol Cancer Res. 2011 Aug. 1) and possibly other agents.

In certain embodiments, the compounds disclosed herein modulate p62 activity in stromal cells which can decrease tumor growth and bone destruction, In particular embodiments, the compounds disclosed herein may be used for inhibiting osteoclastogenesis and/or reducing osteoclast activation. Osteoclast is the primary bone-resorbing cell in both normal and pathologic states. Increased osteoclastic bone resorption can result from both increased osteoclast formation and activation of preformed osteoclasts to resorb bone. In patients with bone metastases, osteolytic bone destruction can result in severe bone pain, pathologic fractures, hypercalcemia, and nerve compression syndromes. Several tumors show a high predilection for bone, including renal cancer, lung cancer, thyroid cancer, prostate cancer, multiple myeloma and breast cancer, see e.g. Roodman, Journal of Clinical Oncology, vol. 19, 2001, p. 3562. Osteoclast formation and activation may also contribute to osteolytic disease and bone loss in individuals suffering from osteoporosis, such as post-menopausal osteoporosis, Paget's disease, rheumatoid arthritis and head and neck squamous cell carcinoma, see e.g. U.S. Pat. No. 7,462,646.

The compounds disclosed may be co-administered with another therapeutic agent, especially another anti-cancer agent. Illustrative chemotherapeutic agents include an EGF-receceptor antagonist, arsenic sulfide, adriamycin, cisplatin, carboplatin, cimetidine, caminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, megestrol, methopterin, mitomycin C, ecteinascidin 743, busulfan, carmustine, lomustine, lovastatin, 1-methyl-4-phenylpyridinium ion, semustine, staurosporine, streptozocin, phthalocyanine, dacarbazine, aminopterin, methotrexate, trimetrexate, thioguanine, mercaptopurine, fludarabine, pentastatin, cladribin, cytarabine, porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarabicin, epimbican, pirarabican, zorubicin, mitoxantrone, bleomycin sulfate, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethasone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine, camptothecin, irinotecan, topotecan, BAY 38-3441, 9-nitrocamptothecin, exatecan, lurtotecan, gimatecan, homocamptothecins diflomotecan and 9-aminocamptothecin, SN-38, ST 1481, karanitecin, indolocarbazoles, protoberberines, intoplicines, idenoisoquinolones, benzo-phenazines and NB-506.

The compounds identified herein may be included in a pharmaceutical composition that includes at least one pharmaceutically acceptable additive such as a carrier, thickener, diluent, buffer, preservative, surface active agent and the like in addition to the agent. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid earners can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The compounds disclosed herein can be administered to subjects by a variety of mucosal administration modes, including by oral, rectal, intranasal, intrapulmonary, or transdermal delivery, or by topical delivery to other surfaces. Optionally, the compounds can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compounds can be administered ex vivo by direct exposure to cells, tissues or organs originating from a subject.

To formulate the pharmaceutical compositions, the compounds can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compounds can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integxity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compounds can be combined with the base or vehicle according to a variety of methods, and release of the compounds can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compounds can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compounds can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compounds can be delivered to a subject in a manner consistent with conventional methodologies associated with management of the disorder for which treatment or prevention is sought. In accordance with the disclosure herein, a prophylactically or therapeutically effective amount of the compound is administered to a subject in need of such treatment for a time and under conditions sufficient to prevent, inhibit, and/or ameliorate a selected disease or condition or one or more symptom(s) thereof.

The administration of the compounds can be for either prophylactic or therapeutic purpose. When provided prophylactically, the compounds are provided in advance of any symptom. The prophylactic administration of the compounds serves to prevent or ameliorate any subsequent disease process. When provided therapeutically, the compound is provided at (or shortly after) the onset of a symptom of disease or infection.

For prophylactic and therapeutic purposes, the compounds can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the compounds will vary according to factors such as the disease indication and particular status of the subject (for example, the subject's age, size, fitness, extent of symptoms, susceptibility factors, and the like), time and route of administration, other drags or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the compound are outweighed in clinical terms by therapeutically beneficial effects. A non-limiting range for a therapeutically effective amount of a compound within the methods and formulations of the disclosure is about 0.01 mg/kg body weight to about 20 mg/kg body weight, such as about 0.05 mg/kcg to about 5 mg/lcg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or—subcutaneous delivery. Dosage can also be adjusted based on the release rate of the administered formulation, for example, of an intrapulmonary spray versus powder, sustained release oral versus injected particulate or transdermal delivery formulations, and so forth.

EXAMPLES

It is known that the marrow microenvironment provides a critical supportive role in MM and enhances both tumor growth and bone destruction through activation of multiple signaling pathways in stromal cells. Sequestosome 1 (p62) plays a key role in the formation of signaling complexes that result in NF-κB, p38 MAPK and PI3K activation in the marrow microenvironment of patients with MM. Deletion constructs of p62 were generated that lacked specific p62 domains: ΔSH2, ΔPB1, ΔZZ, Δp38, ΔTBS and ΔUBA to identify the domains, particular ZZ domain of p62 responsible for increased MM cell growth and osteoclast (OCL) formation mediated by NF-κB and p38 MAPK signaling, as a means to develop inhibitory peptides/molecules as potential therapeutic agents for MM (FIG. 1). These constructs were then transfected into a p62-knockout stromal cell-line and it was found that the ZZ domain of p62 is required for stromal cell support of MM cell growth, increased IL-6, VCAM-1 expression and OCL formation. These results suggest that dominant negative constructs or small molecules that target the ZZ domain of p62 should block p62 function and inhibit support of MM cells and OCL formation by the marrow microenvironment.

Compound 3 (2-[[3,4-bis(phenylmethoxy)phenyl]methylamino]ethanol, structure shown below) was one of the initial in silico screened virtual hits to p62-ZZ domain. Among these biologically validated compounds, compound 3 shows potent inhibition ([IC$_{50}$ value of less than or equal to 5 μM, more particularly 2 μM) to multiple myeloma cells growth with low toxicity to regular stromal cells.

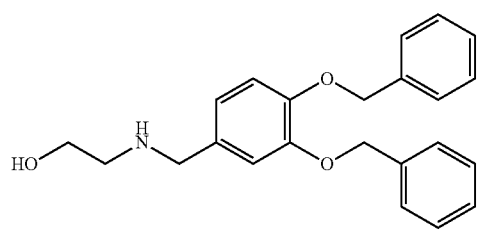

Compound 3: 2-[[3,4-bis(phenylmethoxy)phenyl]methylamino]ethanol (MW:363.45)

Figure 2:
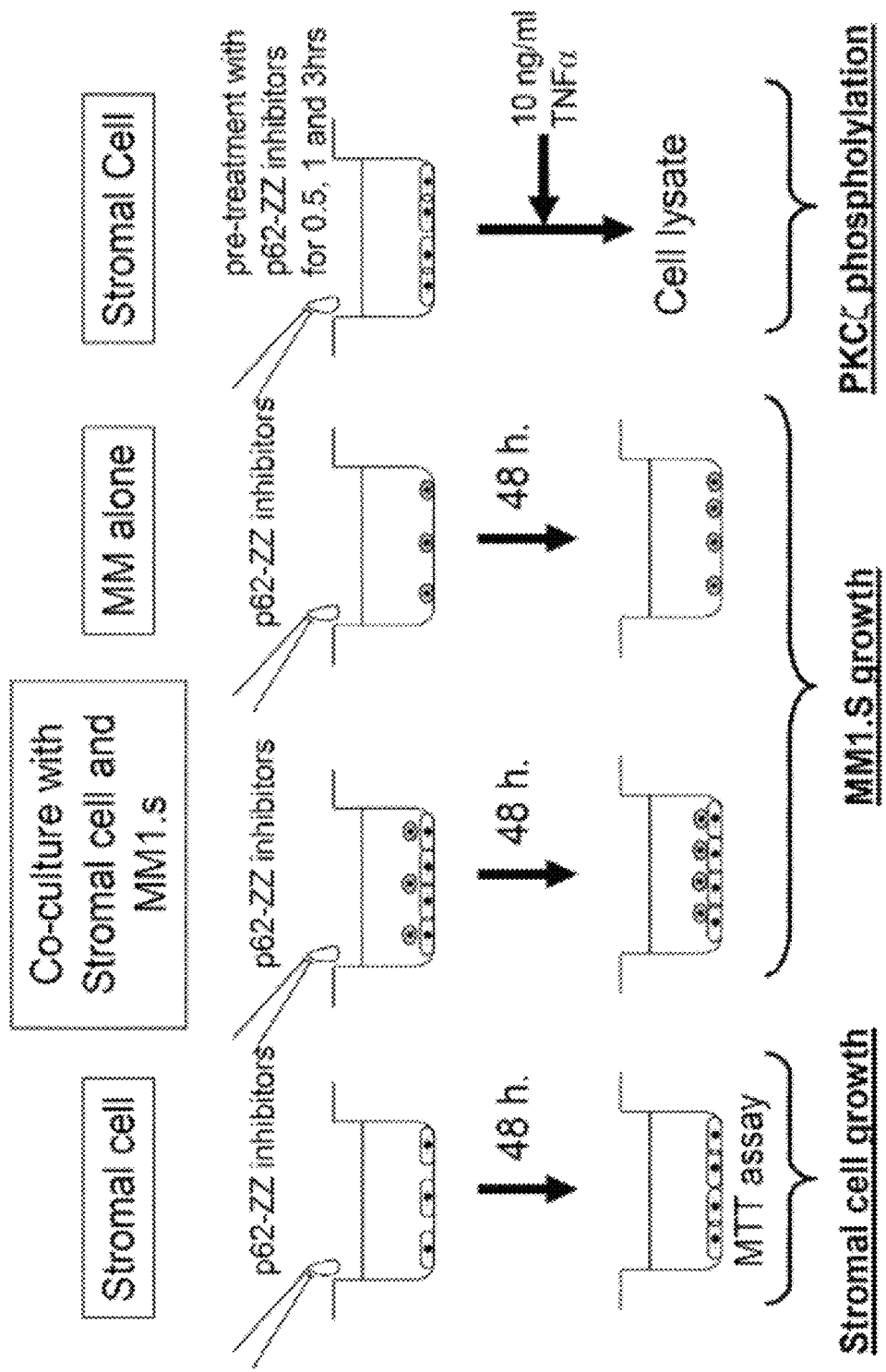
FIG. 2 is a schematic showing in vitro biological assays to validate screened compounds for multiple myeloma cells growth via inhibition of p62-zz domain and PKC phosphorylation.

Systematic biological studies of the inhibitors were performed as shown in FIG. 2. Compound 3 was tested for its capacity to block MM-stimulated signaling in marrow stromal cells, thereby resulting in less bone destruction and MM growth. The effects of the compound 3 on GFP-labeled MM1.S myeloma cell growth with/without stromal cells, IL-6 and VCAM-1 expression on stromal cells induced by TNF-α and OCL formation, and TNF-α induced PKCζ phosphorylation, the specific kinase enzyme activated p62-ZZ, were examined. GFP-labeled MM1.S myeloma cells or normal human CFU-GM, a source of OCL precursors, were then co-cultured with human stromal cells with the p62-ZZ inhibitor. The 10 μM of inhibitor compound 3 blocked MM cell growth by 90% compared to vehicle (0.1% DMSO). This inhibitory compound at 10 μM did not change proliferation of stromal cells by the MTT assay cells. These results show that p62-ZZ inhibitor directly prevents MM cell growth. VCAM-1 expression and IL-6 production induced by TNF-α on stromal cells was blocked by 30% and 90% respectively compared to vehicle levels. Furthermore, TNF-α induced PKC, phosphorylation blocked was in stromal cells and MM1.S when pre-treated with this p62-ZZ inhibitory compound for 3 hours. The results are described in more detail below.

Compounds 1, 2, 4, 5, 6 that were tested in the assays described in the Examples below have the following respective structures:

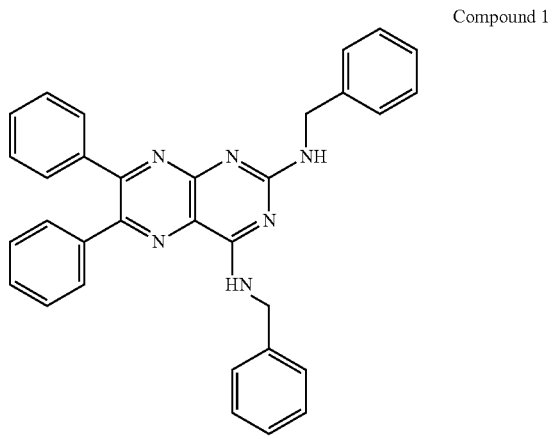

Compound 1

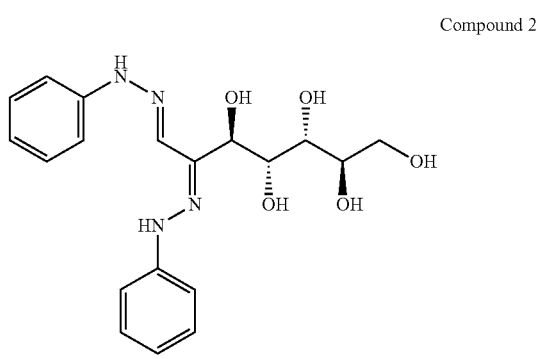

Compound 2

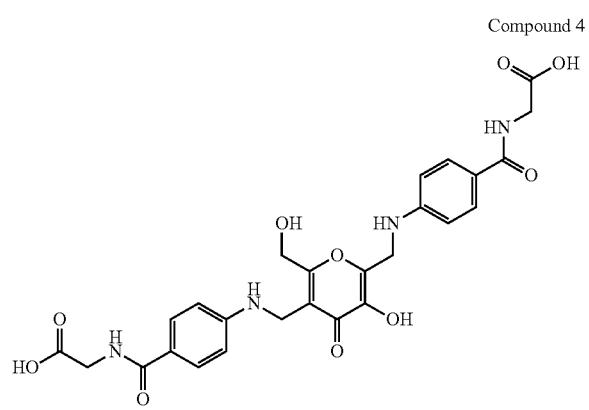

Compound 4

Compound 5

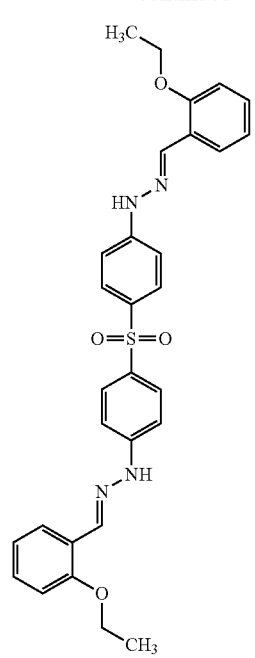

Compound 6

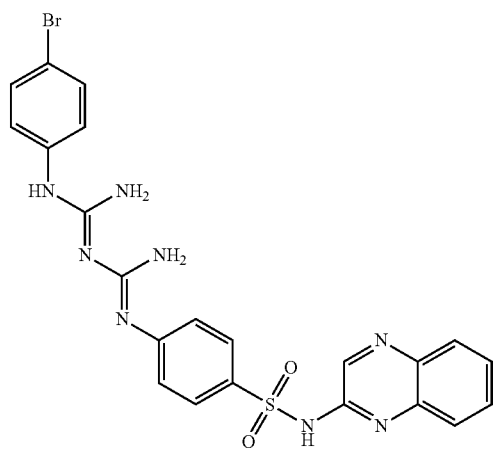 [SMILES: NC(=N\c1ccc(S(=O)(=O)Nc2cnc3ccccc3n2)cc1)/N=C(\N)Nc1ccc(Br)cc1]

Example 1 p62-ZZ Inhibitors Inhibited Myeloma Cell Growth

Figure 3:
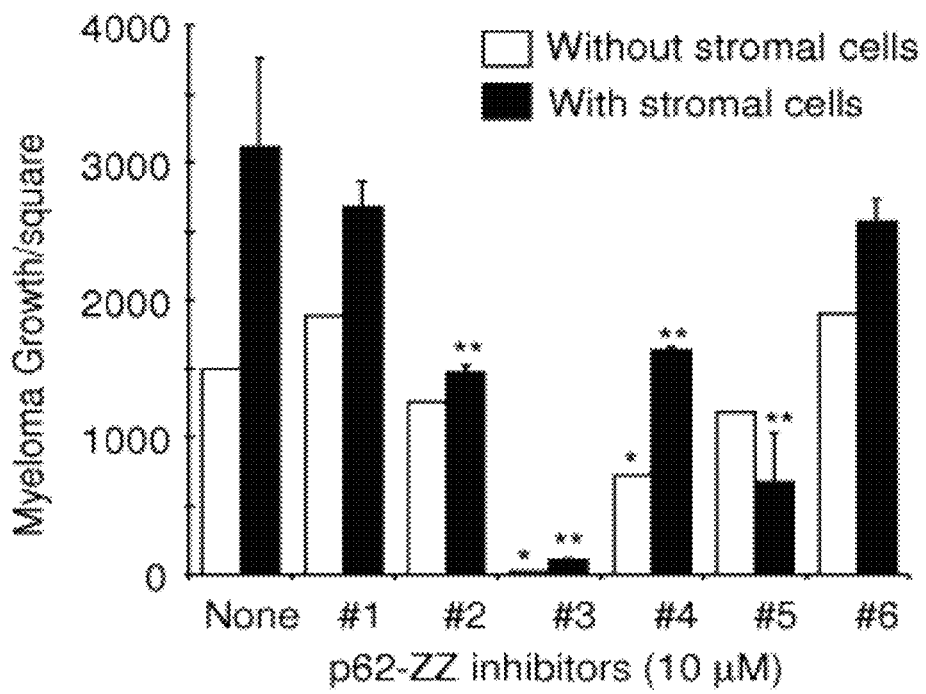
FIG. 3 is a graph depicting MM cell growth inhibition. Data is shown as the mean±SD (n=5). *: P<0.01 compared to no-inhibitor cultures without stromal cells. **: P<0.01 compared to no-treatment co-cultured with stromal cells.

Primary human bone marrow stromal cells were maintained in 10% FCS-IMDM. Stromal cells ($1.5 \times 10^3$ cells/well) were cultured one day prior to the start of co-culture. Green fluorescent protein (GFP)-labeled human myeloma MM1.S cells ($7.5 \times 10^3$ cells/well) were then cultured with/without stromal cells in the presence or absence of the p62-ZZ inhibitors (#1-6) for 72 hours. MM cell growth was determined by fluorescence microscopy. As shown in FIG. 3, p62-ZZ inhibitor #2, 3 and 4 (10 μM) directly blocked MM cell growth. p62-ZZ inhibitor #3 inhibited myeloma cell growth by 90% compared to vehicle. p62-ZZ inhibitor #3 therefor was screened for further testing.

Figure 4A:
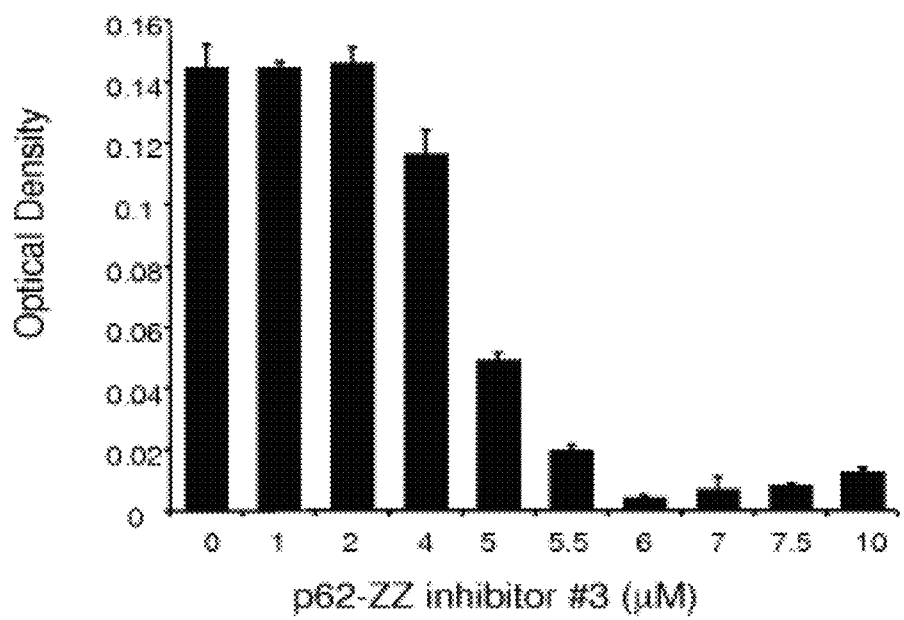
FIG. 4A-C: 4A. Effect of p62-ZZ inhibitor #3 on myeloma cell growth. MM cell growth was assayed by MTT assay. Data are shown as mean±SD (n=5).
Figure 4B:
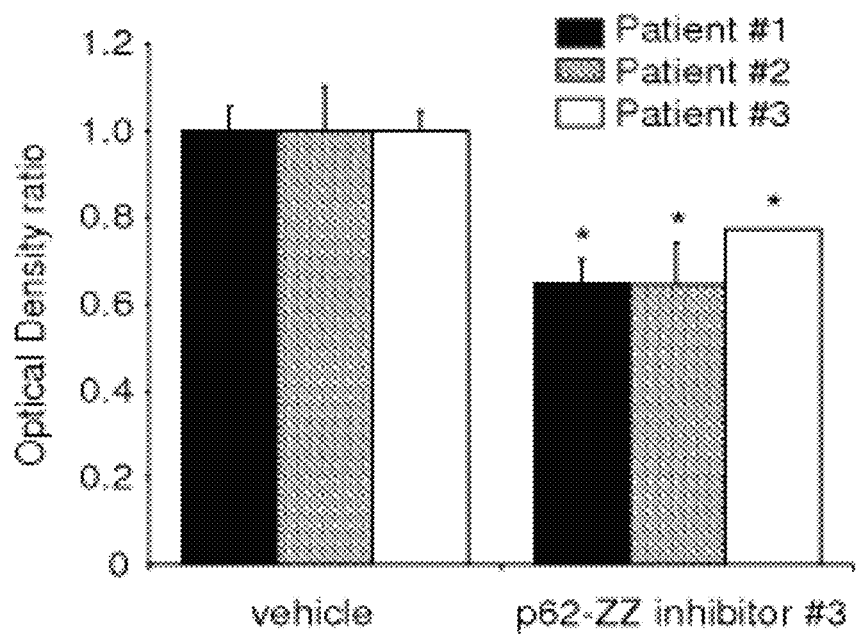
Figure 4C:
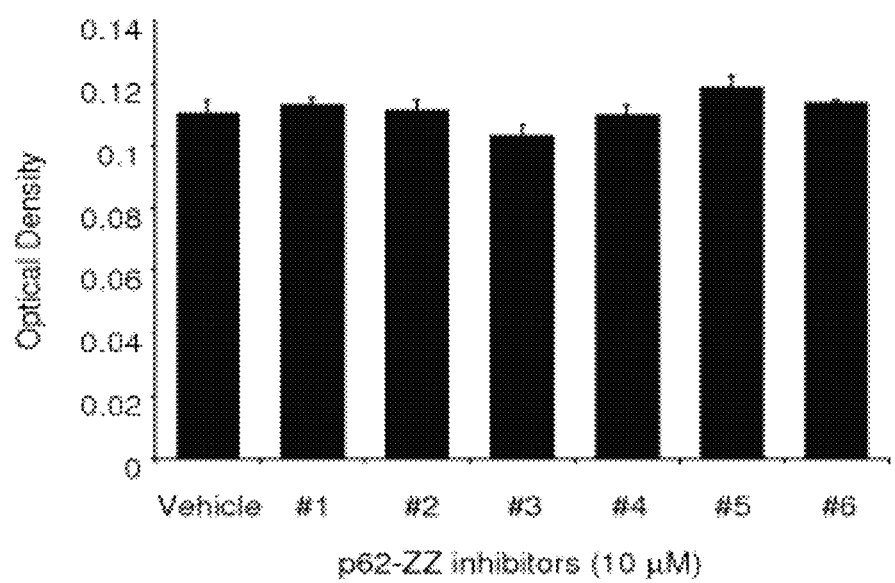

Example 2 p62-ZZ Inhibitor #3 Directly Inhibits MM Cell Growth but Does Not Change Stromal Cell Growth MM1.S ($3 \times 10^5$ cells/well) or CD138 (+) ($1 \times 105$ cells/well) primary myeloma cells were incubated in 96-well plates in the presence of RPMI-1640-10% FCS and various concentrations of p62-ZZ inhibitor #3 at 37° C. 5% CO2 for 48 h to determine the IC50 for inhibiting myeloma cell proliferation. Cell proliferation was measured by MTT assay. p62-ZZ Inhibitor (#3) directly inhibited MM growth of the MM1.S myeloma cell line and CD138(+) primary myeloma cells (FIGS. 4A and 4B), but p62-ZZ inhibitors (#1-6) at 10 μM did not change the proliferation of stromal cells by the MTT assay (FIG. 4C). The IC50 of p62-ZZ inhibitor on MM1.S myeloma cell-line was 6.19 μM.

Example 3

Figure 5A:
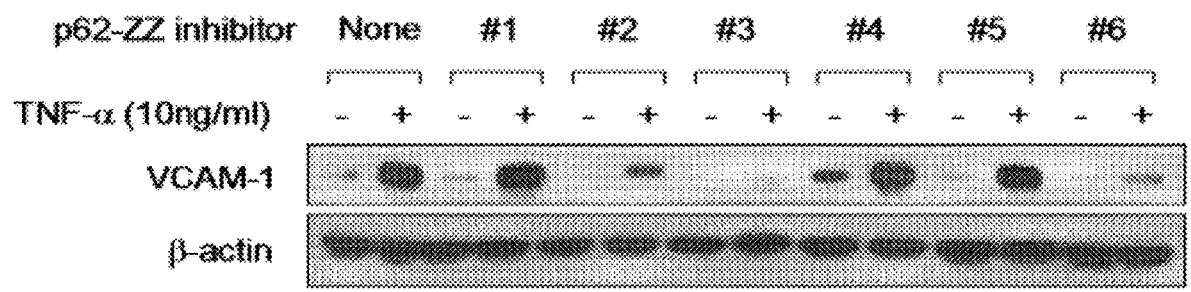
FIG. 5A-B: 5A. VCAM-1 expression using Western blot analysis. Normal human stromal cells were cultured with/without TNF and p62-ZZ inhibitors (#1-6) for 48 hours. The cell lysates were collected and VCAM-1 expression was measured using an anti-VCAM-1 antibody (Santa Cruz).
Figure 5B:
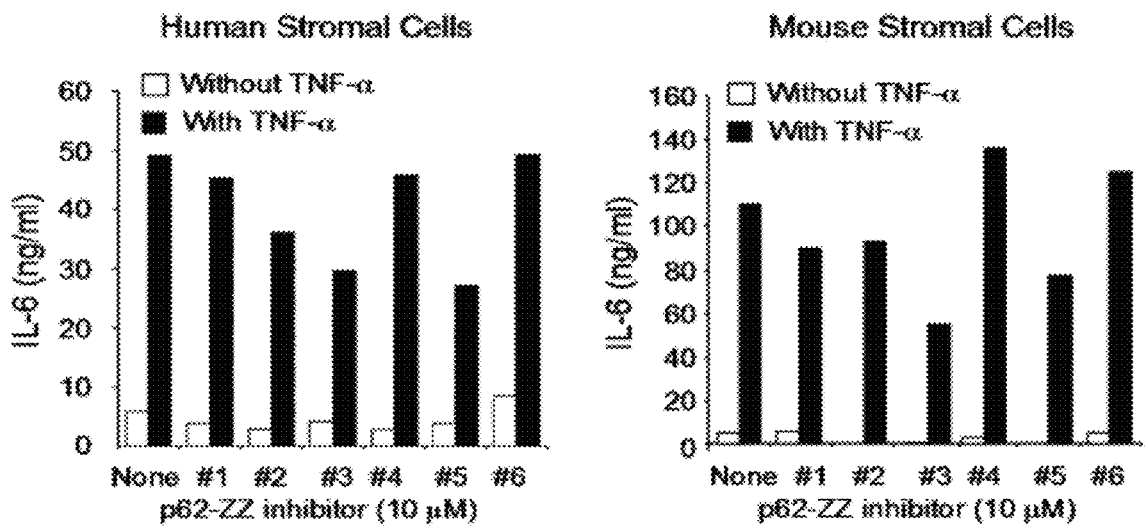
Figure 6:
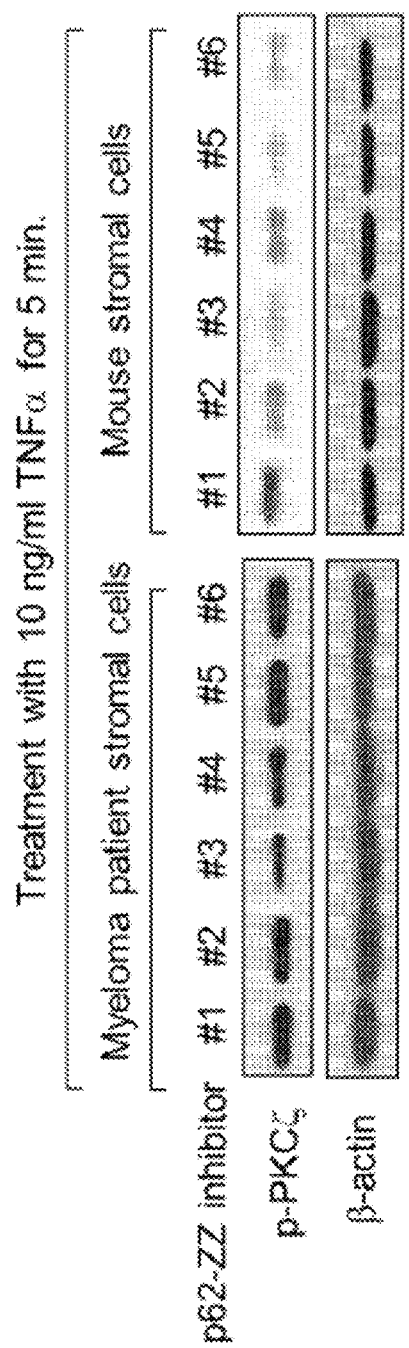
FIG. 6. The effect of p62-ZZ Inhibitors on phospho-PKCζ activation by TNFα stimulated MM patient and mouse marrow stromal cells. For assay of phospho-PKCz, cells were stimulated with 10 ng/ml of TNFα for 5 min and cell lysates were collected. The phospho PKCζ was assayed by Western blot using anti-phospho PKCz anti-body (Cell Signaling).

Effects of p62-ZZ Inhibitors on VCAM-1 Expression and IL-6 Production by Marrow Stromal Cells Normal human or mouse marrow stromal cells were maintained in 10% FBS-IMDM and treated with p62-ZZ inhibitors (#1-6) for 3 hours. Then TNFα or vehicle was added for 48 hours. Cell lysates were collected and VCAM-1 expression measured by Western blot using an anti-VCAM-1 antibody (Santa Cruz). The culture media were collected and IL-6 production was measured using an IL-6 ELISA kit (R&D Company). VCAM-1 expression and IL-6 production by marrow stromal cells induced by TNF-a was blocked by 30% and 90% respectively with addition of p62-ZZ inhibitor #3 compared to vehicle control (FIGS. 5A and B). p62-ZZ inhibitors #2, 3 and 5 blocked IL-6 production by TNF-a stimulated normal human stromal cells (FIG. 5B).

Example 4 p62-ZZ Inhibitor #3 Blocked PKC-Zeta Phosphorylation

Phospho-PKCζ is an unique downstream signal activated by interactions with the p62-ZZ domain. Therefore, we examined whether p62-ZZ inhibitor #3 blocked its phosphorylation. Marrow stromal cells derived from patients with multiple myeloma or mouse stromal cells were cultured in 10% FBS IMDM and then pre-treated with various p62-ZZ inhibitors for 3 hours. For assay of phospho-PKCζ, cells were stimulated with 10 ng/ml of TNF-a for 5 min and the cell lysates were collected. Phospho PKCζ was assayed by Western blot using an anti-phospho PKCζ anti-body (Cell Signaling). TNF-α induced PKCζ phosphorylation in stromal cells was blocked when the cells were pre-treated with p62-ZZ inhibitor #3 for 3 hours.

Example 5 p62-ZZ Inhibitor #3 Blocks Osteoclast (OCL) Formation but not CFU-Blast

Figure 7A:
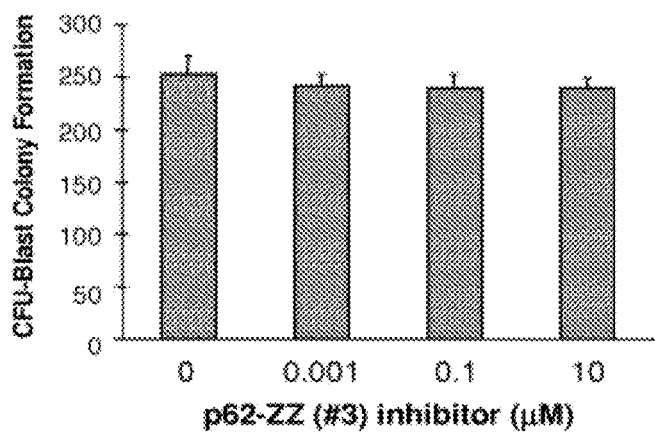
FIG. 7A-C: 7A. CFU-Blast colony formation. Human CD34(+) cells were cultured with p62-ZZ inhibitor #3 and 1 ng/ml of rhIL-3 IL-6 and SCF for 7 days. Data are shown as the mean±SD (n=5).
Figure 7B:
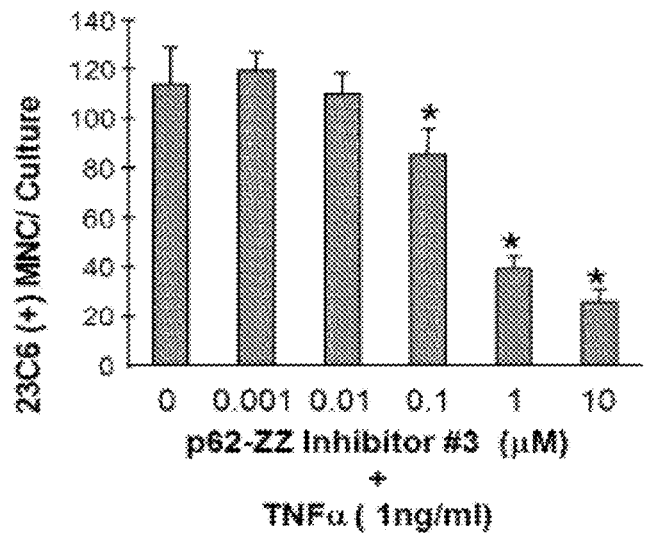

Whether p62-ZZ inhibitor #3 affects hematopoesis since osteoclast precursors are derived from hematopoietic cells was examined. Human CD34(+) mononuclear cells were cultured at 5x103 cells/well in a-MEM containing 1.2% methylcellulose, 30% FBS, 1% deionized BSA, and 1 ng/ml recombinant human IL-3, IL-6 and SC-F (R&D Systems) with or without various concentrations of p62-ZZ inhibitor #3. Cells were plated in a volume of 1.0 ml in 35-mm Petri dishes and incubated at 37° C. in a humidified atmosphere of 5% $CO_2$. Colonies were scored after 7 days of culture using an inverted microscope. As shown FIG. 7A, all concentrations of p62-ZZ inhibitor #3 do not inhibit CFU-Blast colony formation. These results indicate p62-ZZ inhibitor does not block the differentiation of normal hematopoietic precursors, in contrast, p62-ZZ inhibitor #3 blocked human OCL formation dose dependently (FIG. 7B).

Figure 7C:
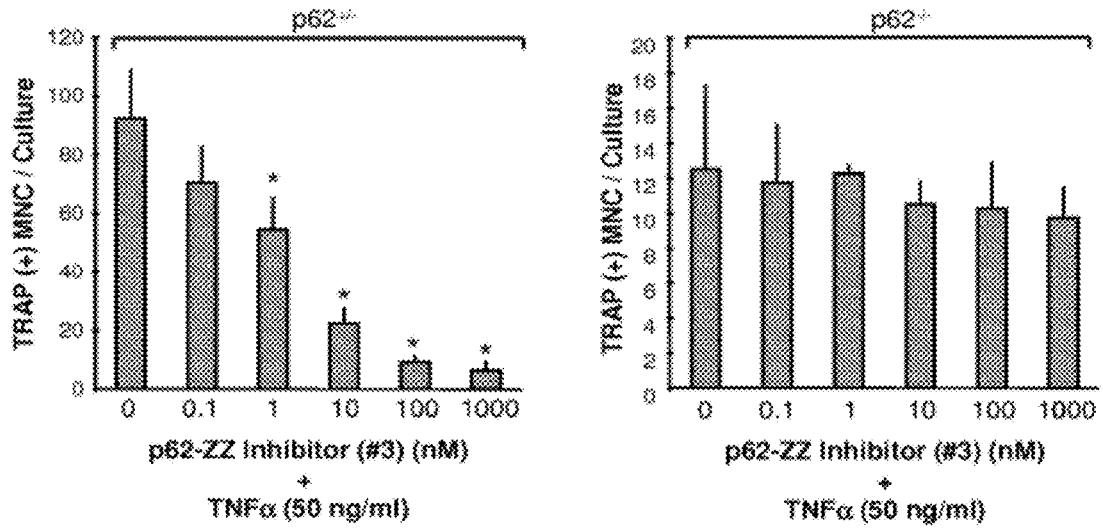
Figure 8:
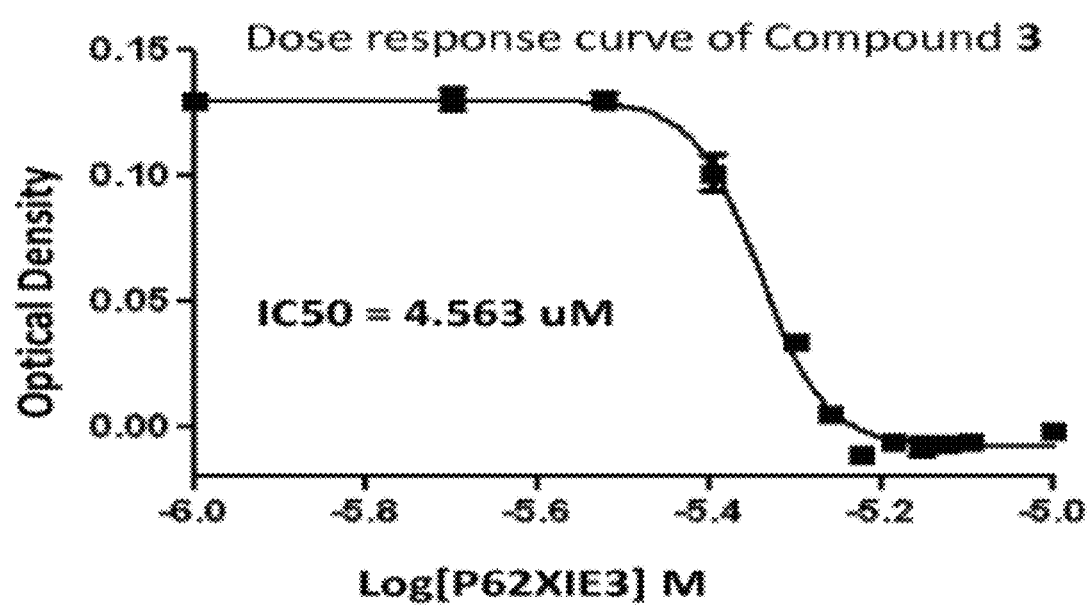
FIG. 8 is a dose response curve for compound 3 (also referred to as compound P62XIE3).

The effects of p62-ZZ inhibitor #3 on osteoclast formation by $p62^{-/-}$ OCL precursors were examined to determine the specificity of the effects of the p62-ZZ inhibitor #3 on osteoclast precursors. CDIIb(+) mononuclear cells from wild type and p62"/_mice were used. CDIIb(+) mononuclear cells ($2.5 \times 10^5$ cells/well) were cultured in α-MEM containing 10% FCS, 50 ng/ml recombinant mouse TNFα and various concentration of p62-ZZ inhibitor #3 for 7 days at 37° C. with 5% $CO_2$ and 95% humidity. On day 7, media were removed and osteoclasts were stained for TRACP (Sigma-Aldrich). OCLs were scored as TRAP positive cells containing 3 or more nuclei. As shown FIG. 7C, p62-ZZ inhibitor #3 blocked OCL formation dose dependently in wild type mice cell cultures. 1 ng/ml of the p62-ZZ inhibitor was the IC50 concentration for wild type cells. In contrast, p62-ZZ inhibitor #3 did not block OCL formation by p62 knockout OCL precursors.

Example 6 p62-ZZ Inhibitor #3 has Been Identified as the Best Lead Compound

Compound #3 will be tested in our well-characterized model of MM bone disease in which 5TGM1 cells that express GFP are injected intratibially and the effects on both MM growth and bone destruction can be quantitated.

In these experiments, the effects of treating animals at the time that the MM cells are injected at 1, 2 or 3 weeks after tumor injection when lytic lesions are well-established and tumor growth is significant in these animals will be determined (Esteve F, et al 2008. Blood (American Society of Hematology): Abstract.). An intratibially route rather than IV or IC administration of MM cells was selected because it allows one to follow localized lesions rather than studying the entire mouse. Briefly, $5 \times 10^5$ 5TGM1-GFP cells in 10 μPBS will be injected intratibially into SCID mice. Control mice will be injected with PBS to control for damage to bone due to injection. At the time of tumor injection, mice will be treated I.P. daily with the appropriate concentrations of the properly formulated inhibitor #3. Tibias from the mice will be analyzed by fluorescence imaging and μCT at 1, 2 and 3 weeks after injection of 5TGM1 cells to assess tumor burden, OCL formation and bone destruction. Alternatively, in studies of the capacity of the p62-ZZ inhibitor #3 to eradicate established tumors, SCID mice will be injected with 5TGM1-GFP cells or saline as described above and the daily injections of p62-ZZ inhibitor #3 will be started 1, 2 or 3 weeks after MM cell injection. Animals will be treated for 3 weeks and then analyzed.

Example 7 p62-ZZ Antagonist (#3) Enhances Apoptosis Markers in MM Cells

Figure 9A:
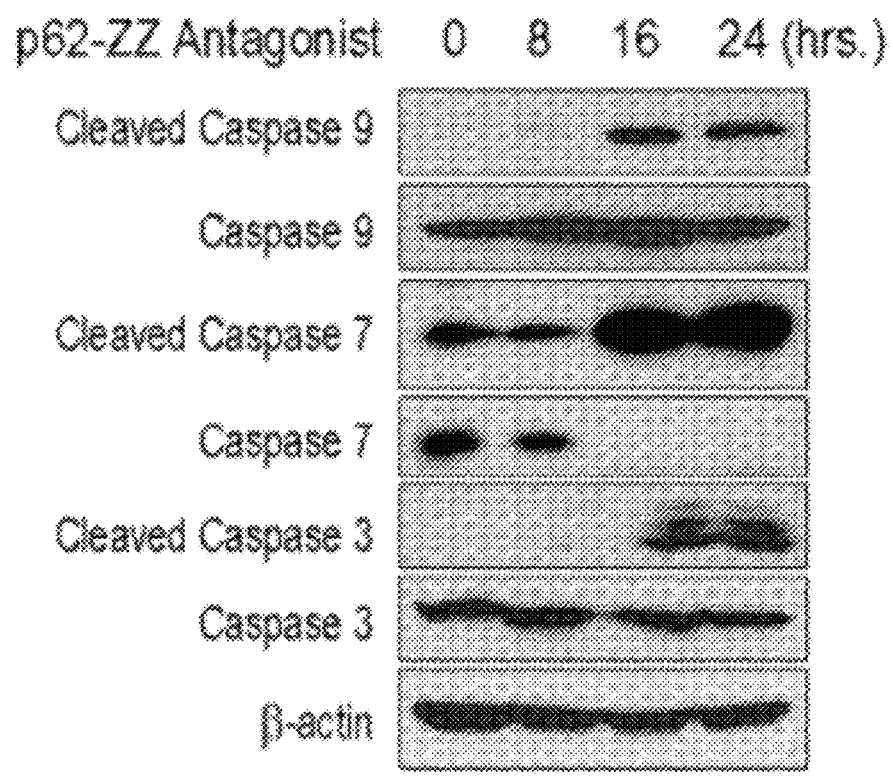
FIG. 9A-C: 9A. The p62-ZZ antagonist induced cleavage of caspase 9, 7 and 3 in MM1.S cells. MM1.S cells were cultured with 10 μM of p62-ZZ antagonist for the indicated time, and then cell lysates were collected. Caspase 9, 7 and 3 were detected by Western blotting using anti-caspase 9, 7 and 3 specific antibodies (Cell Signaling).
Figure 9B:
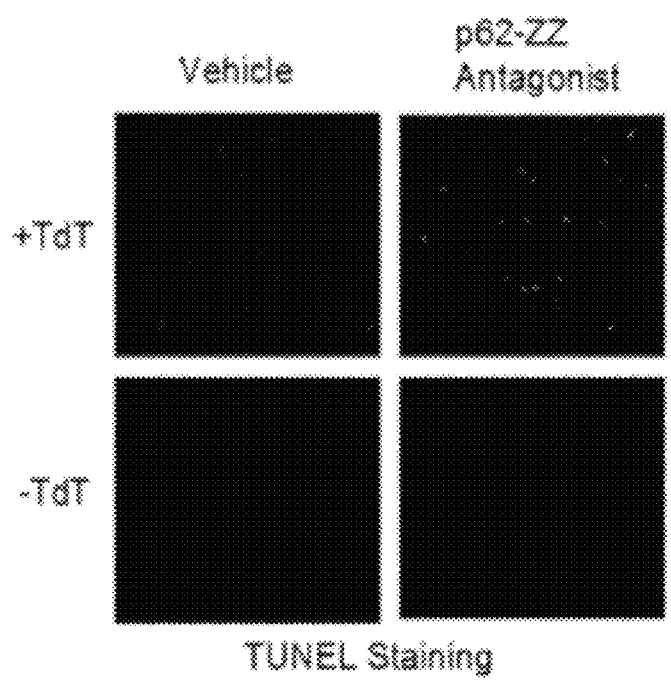
Figure 9C:
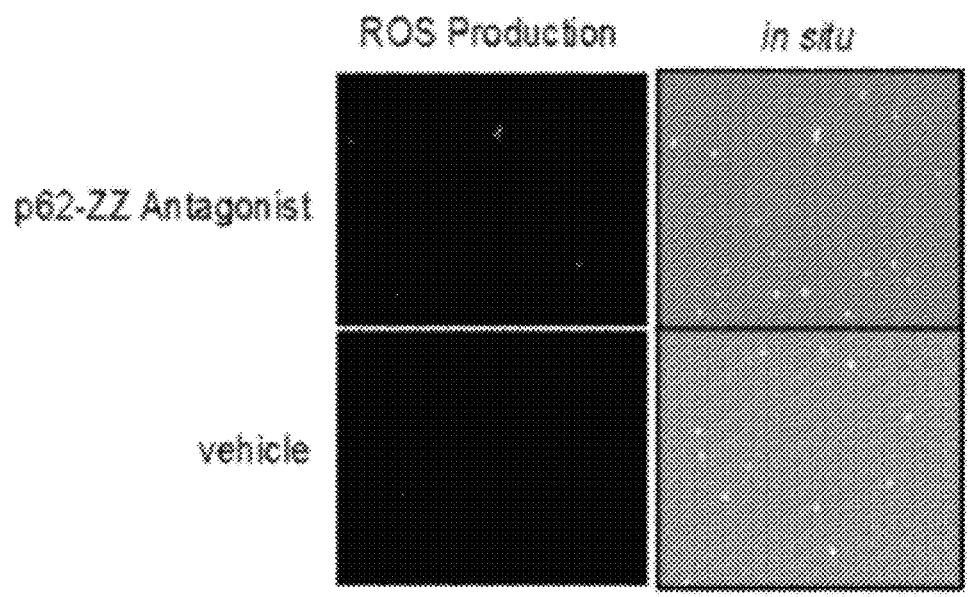

The expression of apoptosis markers in p62-ZZ antagonist treated on 25 MM cells was determined to determine the mechanism action of this antagonist. The p62-ZZ antagonist induced cleavage of caspase 9, 7 and 3 after 16 hours (FIG. 9A) and positive TUNEL staining of cells was induced by the p62-ZZ antagonist after 24 hours (FIG. 9B). The p62-ZZ antagonist induced reactive oxygen species (ROS) production resulting in the inhibition of autophagy which is induced by p62 (FIG. 309C).

Example 8 p62-ZZ Antagonist Does not Show Significant Toxicity In Vivo

Figure 10A:
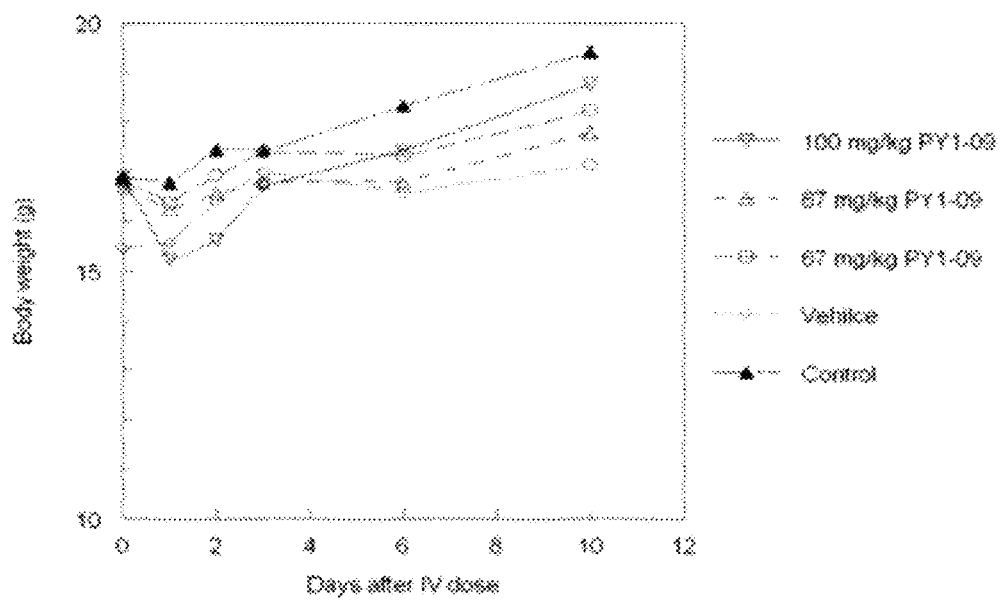
FIG. 10A-D: 10A. Single dose acute toxicity study by Up/Down Methods. Body weights of the mice following dosing.
Figure 10B:
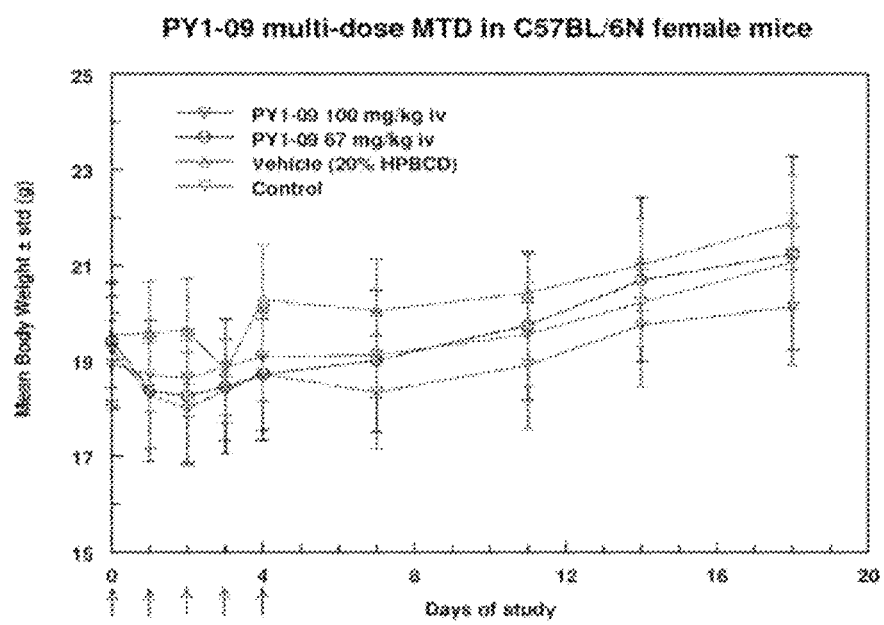
Figure 10C:
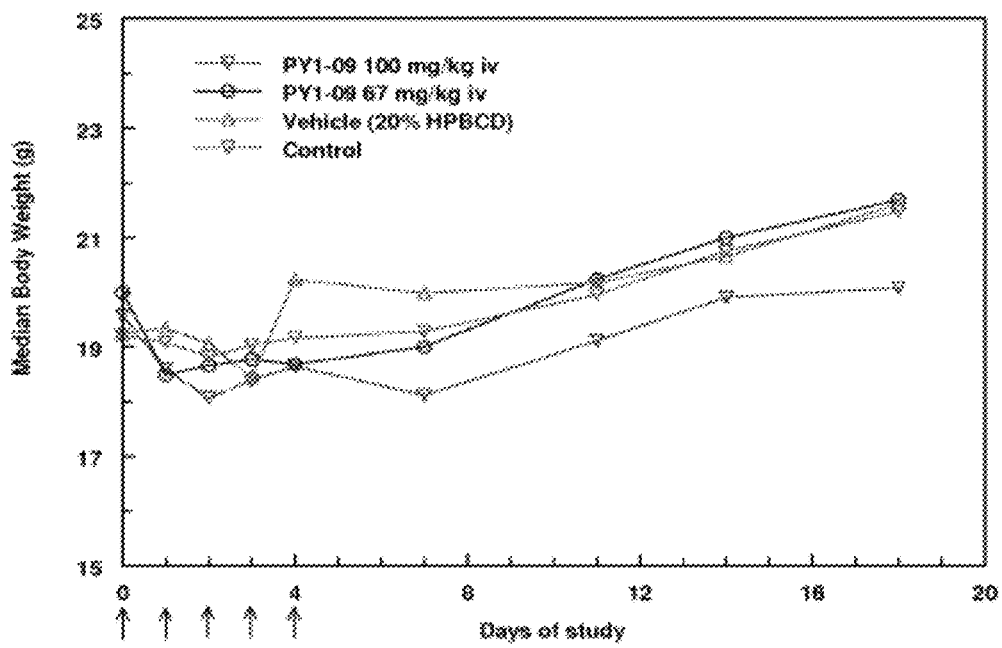
Figure 10D:
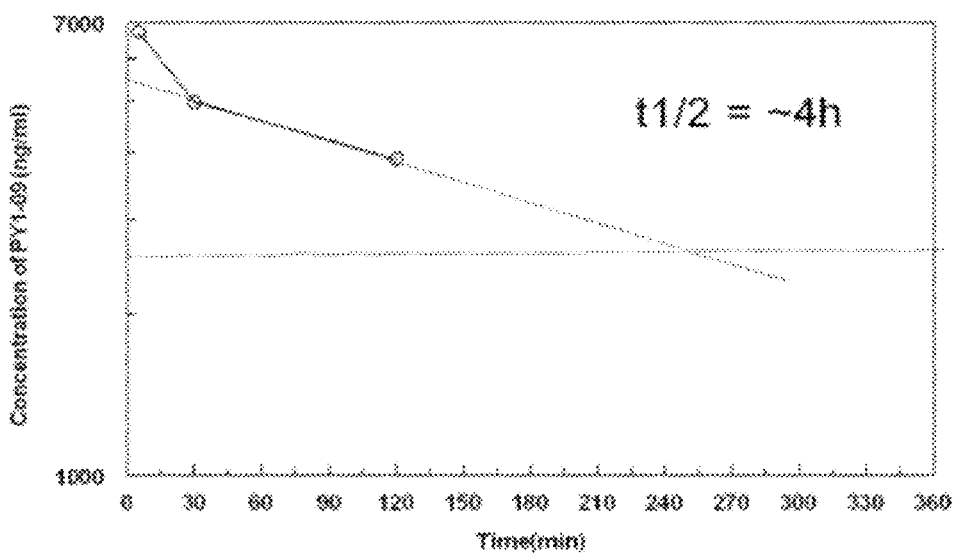

Preliminary in vivo studies of the p62-ZZ antagonist #3 were performed 5 to determine the toxicity, multiple doses MTD and plasma concentration of the antagonist given IV. For the pilot PK study the prototype p62-ZZ antagonist (compound #3) was used as an internal standard for Mass spectroscopy assays. Doses up to 100 mg/kg given either as a single dose (FIG. 10A) or qdx5/day had no effect on body weight for up to 20 days (FIGS. 10B, C). Intravenous injection of 10100 mg/kg of the p62-ZZ antagonist resulted in plasma concentrations of 7000 ng/ml with at ½ of 4 hours (FIG. 10D). Examination of brain, liver, kidney tissue from these mice should no gross pathology. Exploratory metabolic studies showed 3 distinct peaks which likely represent hydroxylation or glucuronidation.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating multiple myeloma in a subject, the method comprising administering to the subject a therapeutically effective amount of at least one p62-ZZ inhibitor compound of structural Formula I:

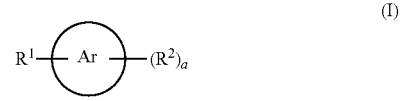

or a pharmaceutically acceptable salt or ester thereof, wherein:
Ar is an arylene or heteroarylene;
$R^1$ has a structure of:

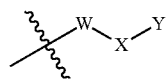

wherein W is an alkanediyl; X is —$NR^5$—, wherein $R^5$ is H; and Y is a hydroxyalkyl, an aminoalkyl, or a carboxylalkyl;
each $R^2$ is the same or different and has a structure of:

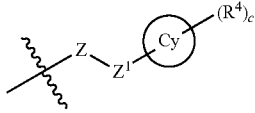

wherein Z is —NR⁶— or —O—; R⁶ is H;
Z¹ is (—CH₂—);
Cy is a 6-membered aryl ring; and
each R⁴ is the same or different halogen; c is 1; a is 2; and
b is 0.

2. The method of claim 1, wherein a first R² group is in a meta position on the Ar ring of Formula I relative to the R¹ group, and a second R² group is in a para position on the Ar ring of Formula I relative to the R¹ group.

3. The method of claim 1, wherein W is —CH₂.

4. The method of claim 1, wherein R² is

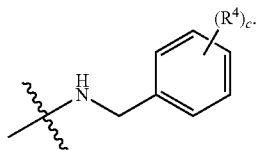

5. The method of claim 1, wherein the p62-ZZ inhibitor is

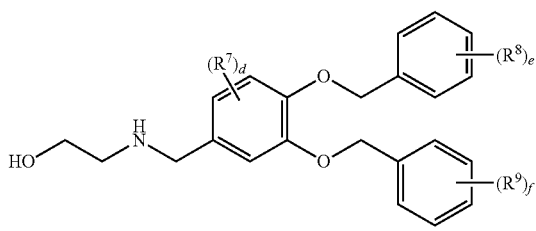

wherein each R⁷, R⁸, and R⁹ are the same or different and are selected from —F or —Cl; d is 0, e is 1, and f is 1.

6. The method of claim 1, wherein the multiple myeloma is drug resistant multiple myeloma.

7. The method of claim 1, further comprising co-administering at least one anti-cancer agent with the p62-ZZ inhibitor.

8. The method of claim 7, further comprising inhibiting osteoclastogenesis and/or reducing osteoclast activation.

9. A method of inhibiting multiple myeloma cell growth, comprising contacting multiple myeloma cells with a compound, or a pharmaceutically acceptable salt or ester thereof, having a formula I of:

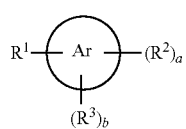

or a pharmaceutically acceptable salt or ester thereof, wherein:
Ar is an arylene or heteroarylene;
R¹ has a structure of:

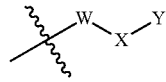

wherein W is an alkanediyl; X is —NR⁵—, wherein R⁵ is H; and
Y is a hydroxyalkyl, an aminoalkyl, or a carboxyalkyl;
each R² is the same or different and has a structure of:

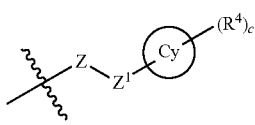

wherein Z is —NR⁶— or —O—; R⁶ is H;
Z¹ is (—CH₂—);
Cy is a 6-membered aryl ring; and
each R⁴ is the same or different halogen; c is 1; a is 2; and b is 0.

10. The method of claim 9, wherein a first R² group is in a meta position on the Ar ring of Formula I relative to the R¹ group, and a second R² group ins in a para position on the Ar ring of Formula I relative to the R¹ group.

11. The method of claim 9, wherein W is —CH₂.

12. The method of claim 9, wherein R² is

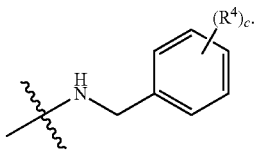

13. The method of claim 9, wherein the p62-ZZ inhibitor is

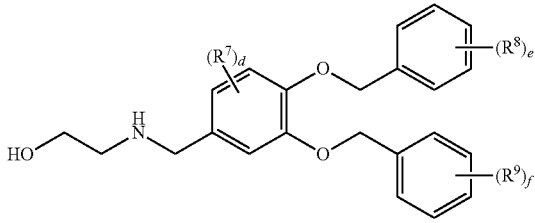

wherein each R⁷, R⁸, and R⁹ are the same or different and are selected from —F or —Cl; d is 0, e is 1, and f is 1.

14. The method of claim 1, wherein W is —CH₂, X is —NR⁵, and R is H.

15. The method of claim 1, further comprising co-administering at least one anti-cancer agent with the p62-ZZ inhibitor.

16. The method of claim 15, further comprising inhibiting osteoclastogenesis and/or reducing osteoclast activation.

17. The method of claim 9, wherein W is —CH₂, X is —NR⁵, and R is H.

* * * * *